United States Patent [19]

Fedorov et al.

[11] Patent Number: 4,838,890
[45] Date of Patent: Jun. 13, 1989

[54] INTRAOCULAR PROSTHETIC LENS

[76] Inventors: Svyatoslav N. Fedorov, ulitsa Dostoevskogo,12,kv.32; Eleonora V. Egorova, ulitsa Kuusinena, 15,kv.44; Natalya A. Strusova, ulitsa Supruna, 4/10, kv.78; Viktor I. Glazko, ulitsa 26 Bakinskikh komissarov,12,korpus 4,kv.66; Vladimir N. Trubilin, 4 Samo techny pereulok,3,kv.31, all of Moscow, U.S.S.R.

[21] Appl. No.: 228,541

[22] Filed: Aug. 4, 1988

[51] Int. Cl.[4] ............................................. A61F 2/16
[52] U.S. Cl. ........................................................ 623/6
[58] Field of Search ............................................ 623/6

[56] References Cited

U.S. PATENT DOCUMENTS

| 4,242,760 | 1/1981 | Rainin | 623/6 |
| 4,251,887 | 2/1981 | Anis | 623/6 |
| 4,581,032 | 4/1986 | Grandon | 623/6 |
| 4,687,484 | 8/1987 | Kaplan | 623/6 |

FOREIGN PATENT DOCUMENTS 1271505  11/1986  U.S.S.R. ................................. 623/6

OTHER PUBLICATIONS

The Journal of the American Academy of Ophthalmology, vol. 89, No. 8S, Aug. Supplement 1982 (3 pages), pp. 148 and 172.

Primary Examiner—Ronald L. Frinks

[57] ABSTRACT

The intraocular prosthetic lens comprises an optical lens and two diametrally opposite loop-shaped support elements. Each of the support elements is made up of two mutually intersecting arches which are fastened together with the optical lens through one of their ends. The ends of the arches adjoining the optical lens are straight-line and are set at an angle of 105 to 115 degrees to each other. The ratio of the radius of curvature of the free curvilinear ends of the arches to a maximum overall length of the intraocular prosthetic lens lies within 0.16 and 0.21.

1 Claim, 1 Drawing Sheet

INTRAOCULAR PROSTHETIC LENS

TECHNICAL FIELD

The invention relates generally to medicine, more specifically to ophthalmology, and has particular reference to an intraocular prosthetic lens.

The present invention can find application for treatment of cataract of any etiology except for traumatic one.

DESCRIPTION OF THE PRIOR ART

Known in the present state of the art is an intraocular prosthetic lens, comprising an optical lens and two diametrally opposite support elements which are shaped as arches, each being held, with one of its ends, to the optical lens. The arch portion adjacent to its end secured to the optical lens is straight-line and has a considerable length. The support elements are so fastened together with the optical lens that the straight-line portions of the arches are parallel to each other and to the longitudinal axis of symmetry of the intraocular prosthetic lens (cf. the journal 'Opthalmology', August 1982, p.148, Model 17, 17A).

However, the heretofore-known state-of-the-art intraocular prosthetic lens is featured by a rigid construction which is due to the provision of considerable-length straight-line portions in the support elements, arranged parallel to the longitudinal axis of symmetry of the intraocular prosthetic lens. This leads to an extended time spent for implantation of the intraocular prosthetic lens, to higher traumatism of the surgical procedure, i.e., the danger of inflicting injury upon the ocular tissues with the free ends of the arches both in the course and after surgery. Besides, such a rigid construction is of low versatility so that an intraocular prosthetic lens is to be selected to suit the size of the patient's eye.

Another prior-art intraocular prosthetic lens is known to comprise an optical lens and two diametrally opposite support elements shaped as curvilinear arches which are made of an elastic material (cf. the journal 'Opthalmology', August 1982, p.148, Model 20, 20A).

The aforesaid construction of the intraocular prosthetic lens is more elastic, more easily implantable and more versatile. However, implantation of such a construction of the intraocular prosthetic lens is also fraught with an injury to the ocular tissues with the free ends of the arches. Apart from this, since the optical lens is fastened together with each of the support element only at a single point, there is possible a turn of the lens about an axis passing through said points, with the result that the 'pupil catching' syndrome occurs which cannot be eliminated without repeated operative intervention.

Still one more intraocular prosthetic lens is known to use heretofore, comprising an optical lens and two diametrally opposite loop-shaped support elements, each being fastened together with the optical lens through their both ends. The support elements are bean-shaped and their end portions directly adjoining the optical lens are practically parallel to each other (U.S. Pat. No. 4,251,887). This construction of an intraocular prosthetic lens has no open sharp ends that might inflict damage upon the ocular tissues; besides, the danger of the 'pupil catching' syndrome is minimized, since the given construction is a relatively rigid one having closed loops as the support elements. An additional contrivance, i.e., a container is employed for implanting the intraocular prosthetic lens of the construction in question, into which it is put in a compressed state, as well as a pusher for the prosthetic lens to displace from the container into the patient's eye. Implantation of such an intraocular prosthetic lens requires a great many manipulations on the part of the surgeon, which extends the operating time, increases the percent of lost endothelial cells. A large portion of the support element arc contacting the ocular tissue might result, in case some additional tissues such as adhesions, scars, dense masses of the patient's own crystalline lens are present in the zone of setting the support elements, in decentration of the optical lens being implanted and hence in some visual disorders, such as, e.g., double image.

In addition, it is due to rigidity of the known construction that renders it low versatile.

SUMMARY OF THE INVENTION

It is an object of the invention to render implantation of an intraocular prosthetic lens less traumatic.

It is another object of the invention to provide wide versatility of the construction of an intraocular prosthetic lens.

It is one more object of the invention to reduce the number of surgeon's manipulations and to cut down the operating time spent for implantation of an intraocular prosthetic lens.

The essence of the invention resides in that in an intraocular prosthetic lens, comprising an optical lens and two diametrally opposite loop-shaped support elements fastened together with the optical lens through their ends, according to the invention, each of the support elements is made up of two coplanar mutually intersecting arches, each having the ends which are at the same time the ends of the loop-shaped support elements, said ends of the arches being secured to the optical lens; the portions of the arches immediately adjoining the optical lens are straight-line and are set at an angle of 105 to 115 degrees to each other in each of the support elements, while the ratio of a radius of curvature of the free curvilinear ends of the arches to a maximum overall length of the intraocular prosthetic lens falls within 0.16 and 0.21.

An intraocular prosthetic lens, according to the present invention, is instrumental in minimizing the traumatic lesion inflicted upon the ocular tissues, since the free ends of the arches are situated inside the loop of the support elements, and the ocular tissues are protected against their harmful effect by the outer contour of the support element loop. Inasmuch as each of the support elements of the intraocular prosthetic lens, according to the invention is made up of two elastic elements, viz., arches which are not rigidly interconnected, the support elements are in fact featured by adequately high elasticity so that the intraocular prosthetic lens requires no additional contrivances for being implanted in a patient's eye, and its implantation involves a minimum number of manipulations to be performed by the surgeon. The construction of the intraocular prosthetic lens, according to the invention is characterized by broad versatility, this being due to high elasticity of its support elements.

BRIEF DESCRIPTION OF THE DRAWINGS

In what follows the invention is illustrated by a detailed description of a specific exemplary embodiment thereof with reference to the accompanying drawings. wherein according to the invention.

DETAILED DESCRIPTION OF THE INVENTION

Figure 1:
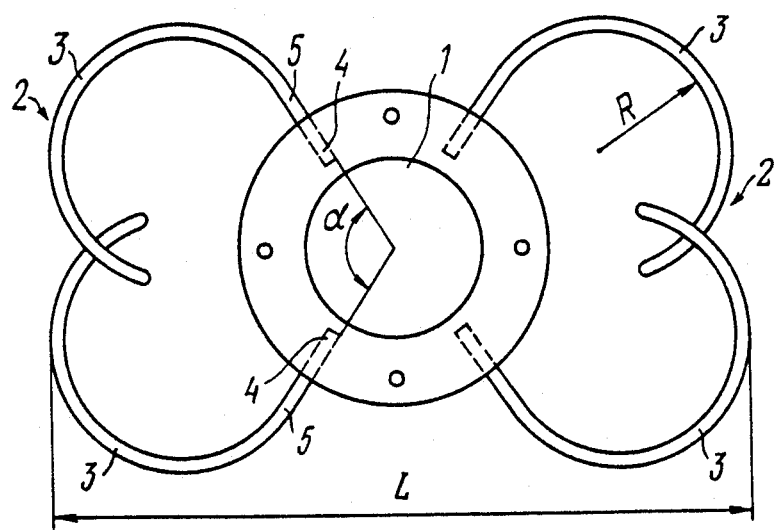
FIG. 1 is a schematic plan view of an intraocular prosthetic lens.
Figure 2:
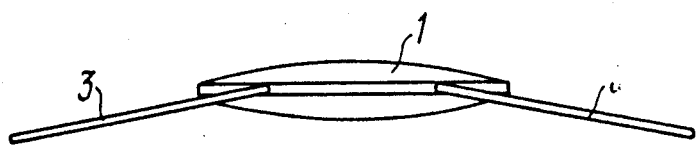
FIG. 2 is a side view of FIG. 2.

The intraocular prosthetic lens as shown in FIGS. 1 and 2 comprises a biconvex circular lens 1 and two diametrally opposite loop-shaped support elements 2 fastened together with the lens 1 through their both ends. The support element 2 consists of two coplanar mutually intersecting open arches 3 which are held together with the lens 1 through their one ends 4 serving at the same time as the ends of the support elements 2. Portions 5 immediately adjoining the lens 1 are straight-line and are set at an angle α ranging within 105 and 115 degrees to each other in each of the support elements 2. A radius R of curvature of the free curvilinear ends of the arches 3 stands to a maximum overall length L of the intraocular prosthetic lens as 0.16 through 0.21.

Should the magnitude of the angle α be below 105 degrees, this will result in a reduced general area of an intraocular prosthetic lens and hence a reduced contact area of the prosthetic lens with the posterior eye capsule; the resilience of the support elements 2 is also affected and their contact area with the periphery of the capsular arc. All this as a whole will lead to decentration and rotation of the optical lens 1 in the pupillary region and hence to impaired vision due to astigmatism and a prismatic effect.

If the magnitude of the angle α exceeds 115 degrees this will bring about an increase in the total area of the intraocular prosthetic lens and hence a larger operative incision, prolonged operating time due to difficulties encountered in implanting the intraocular prosthetic lens and its centration, heavier traumatic lesion of the ocular tissues involved, and a possible danger of the subjacent ocular tissues becoming cut through by the support elements.

The ratio of the radius R of curvature of the bent ends of the arches 3 to the maximum overall length L of the prosthetic lens may not be less than 0.16, since otherwise a total area of the prosthetic lens will be reduced and, accordingly, the contact area with the posterior capsule and the periphery of the capsular arc. This may result in decentration of the intraocular prosthetic lens, thus affecting badly the acuity of vision due to the onset of astigmatism and a prismatic effect, which are but hardly amenable to correction.

Conversely, when the R/L ratio is in excess of 0.21 this will result in a larger total area of the intraocular prosthetic lens, a prolonged time for its implanting, and heavier traumatic lesion of the ocular tissues both during surgery and thereafter due to higher elasticity of the support elements 2 and hence higher degree of pressure exerted by them upon the ocular tissues. Furthermore a possible danger of the support elements 2 getting onto the iridal root and the ciliary body, both featuring increased sensitivity to any mechanical irritation. This in turn adds to a postoperative inflammation and to a possible danger for the subjacent tissues to be cut through by the supporting elements due to an excess pressure exerted even through the lens capsule.

The optical lens 1 can be made of, e.g. polymethylmethacrylate.

The support elements can be made of, e.g., polyamide or lavsan.

The implantation technique of the herein-proposed intraocular prosthetic lens is as follows.

Once the conjunctiva and the sclera have been cut through along the limbus and the pupil has been dilated by medication of a one-percent Mesaton (phenylephrine hydrochloride) solution, the anterior capsulotomy and extracapsular cataract extraction is carried out. Then the intraocular prosthetic lens is gripped with a forceps of any construction, e.g., that for tying-up sutures, and introduced into the anterior eye chamber guiding one of the support elements 2 through the pupil, under the iris and into the inferior capsular sac. Once one of the support elements 2 has been introduced the forceps is to be withdrawn from the ocular chamber. Then the reposition of the other support element 2 is carried out by alternatively introducing its arches 3 by their bending towards the optical lens 1 and putting them into the superior capsular sac behind the iris. The surgery is terminated with contracting the pupil by an acetylcholine solution medicated into the aqueous humor of the anterior chamber, hermetization of the latter and restoring its depth to 3.0 mm using an isotonic physiological saline.

It is due to the fact that the arches 3 are fastened together with the optical lens 1 to define an angle α ranging within 105 to 115 degrees between the straight-line portions 5 of the arches, as well as due to the fact that each of the support elements 2 is made up of two open arches 3, that the support elements 2 are featured by relatively high elasticity and adequate flexibility, which facilitates their compression, during the implantation procedure, with the aid of a conventional forceps without resorting to any additional contrivances, contributes to curtailed operating time and to lower degree of traumatism of the surgical procedure, as well as provides for a stable central position of the optical lens 1 even in case some additional tissues are present in the implantation zone.

Thanks to the fact that the free ends of the arches 3 are situated within the loops of the support elements 2 and are protected by their contours, any danger of traumatic lesion inflicted upon the ocular tissues by said ends both in the course of implantation of the optical lens (since the latter is free to slide) and after surgery is eliminated.

The fact that the support elements 2 are made sectional and consist each of the two flexible open arches 3 imparts broad versatility to the intraocular prosthetic lens, according to the invention. With the same size of the intraocular prosthetic lens the optical lens 1 is reliably centred and stably retained in the centred position irrespective of the size of the eye being operated upon due to selective deformation of the support elements 2.

Considered below are some specific examples of practical implantation of the herein-proposed intraocular prosthetic lens, according to the invention.

EXAMPLE 1

Male patient, aged 40 was admitted to the eye department of a hospital with the diagnosis:total contusion cataract of the left eye. Visual acuity on admission:

Right eye - 1.0

Left eye - 0.03

Extracapsular cataract extraction was carried out accompanied by intracapsular implantation of the intraocular prosthetic lens, according to the invention. Both the surgery and the postoperative period were uneventful.

On the fourth day after surgery the patient was dismissed from the hospital, the visual acuity of the left eye being 0.15 with a sphere of +1.5 D=0.3 to 0.4. A month later the visual acuity was restored to 1.0 with a correction by a sphere of +1.0 D and has been retaining for the following six months.

EXAMPLE 2

Female patient, aged 50 was admitted to the eye department of a hospital with the diagnosis: mature complicated cataract. Visual acuity on admission: right eye - 0.03; left eye - 0.2 to 0.3.

Extracapsular cataract extraction was carried out accompanied by intracapsular implantation of the intraocular prosthetic lens into the right eye. Both the surgery and the postoperative period were uneventful. On the third day after surgery the patient was discharged, the visual acuity of the right eye being 0.15, and 0.3 with a dia. 1.5-mm diaphragm. In 1.5 months after surgery the visual acuity was restored stably to 1.0.

Implantation of the hereinproposed intraocular prosthetic lens is indicated following an extracapsular cataract extraction, viz., congenital, complicated, senile, and traumatic cataract with retained shape and volume.

Implantation of the hereinproposed intraocular prosthetic lens is contraindicated in cases where the anterior eye capsule has been injured during surgery.

Application of the herein-proposed intraocular prosthetic lens makes it possible to cut down the operating time by about 35 or 40 percent. Besides, the degree of traumatic lesion of the corneal endothelium (i.e., loss of the endothelial cells) is reduced by about 20 percent, this being due to facilitated introduction of the support elements, as well as owing to the fact that the construction of the support elements of the prosthetic lens enables a lower-diameter optical lens to be employed.

What is claimed is:

1. An intraocular prosthetic lens, comprising:
   —an optical lens;
   —two loop shaped support elements arranged oppositely to each other and each having two ends which are fastened together with said optical lens;
   —two pairs of arches made of an elastic material, each of said pairs establishing one of said support elements;
   —a first end of each of said arches being at the same time one of said ends of the support element, fastened together with said optical lens;
   —a portion of each of said arches directly adjoining its said first end and being essentially straight-line;
   —a second curvilinear end of each of said arches, which is essentially a free end;
   —said arches in each of said pairs being coplanar and said free curvilinear second ends thereof mutually intersecting;
   —said straight-line portions of the arches in each of said support elements being set at an angle of 105 to 115 degrees to each other;
   —a radius of curvature of said free curvilinear second ends of the arches standing to a maximum overall length of said optical lens with said support elements as 0.16 to 0.21.

* * * * *